United States Patent
Schauf et al.

(10) Patent No.: US 9,044,196 B2
(45) Date of Patent: Jun. 2, 2015

(54) AUTOMATED HEART RATE DETECTION FOR 3D ULTRASONIC FETAL IMAGING

(75) Inventors: Michael Schauf, Bothell, WA (US); Keith Johnson, Lynnwood, WA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 13/702,254

(22) PCT Filed: Apr. 27, 2011

(86) PCT No.: PCT/IB2011/051853
§ 371 (c)(1),
(2), (4) Date: Dec. 5, 2012

(87) PCT Pub. No.: WO2011/158136
PCT Pub. Date: Dec. 22, 2011

(65) Prior Publication Data
US 2013/0085393 A1    Apr. 4, 2013

Related U.S. Application Data

(60) Provisional application No. 61/355,885, filed on Jun. 17, 2010.

(51) Int. Cl.
A61B 8/00 (2006.01)
A61B 8/02 (2006.01)
A61B 8/08 (2006.01)
(Continued)

(52) U.S. Cl.
CPC . *A61B 8/543* (2013.01); *A61B 8/02* (2013.01); *A61B 8/0866* (2013.01); *A61B 8/0883* (2013.01); *A61B 8/4405* (2013.01); *A61B 8/483* (2013.01); *A61B 8/5223* (2013.01); *G01S 7/52073* (2013.01); *G01S 7/52074* (2013.01); *G01S 15/8993* (2013.01); *A61B 8/14* (2013.01);
(Continued)

(58) Field of Classification Search
None
See application file for complete search history.

(56) References Cited

U.S. PATENT DOCUMENTS 5,997,479 A    12/1999    Savord et al.
6,139,500 A    10/2000    Clark
(Continued)

FOREIGN PATENT DOCUMENTS

JP    2000135217 A    5/2000
JP    2006102489 A    4/2006
(Continued)

OTHER PUBLICATIONS

Chaoui R et al: "Three and four dimensional fetal echocardiography", Springer, Berlin, DE, vol. 39, No. 1, Jan. 1, 2006, pp. 15-24, XP019323083, ISSN: 1433-0393.
(Continued)

*Primary Examiner* — Unsu Jung
*Assistant Examiner* — Joel Lamprecht (57) ABSTRACT

An ultrasound system and method provide a workflow to acquire 3D images of the fetal heart gated by a synthetic heart gating signal. An ROI is defined in an ultrasound image which delineates the fetal heart. The ultrasound system is controlled to automatically estimate the fetal heart rate from echo signals received from the ROI. When the system has acquired a stable synthetic heart rate signal, an indication thereof is given to the user and the user then commands the system to acquire 3D fetal heart images for a number of fetal heart cycles which are gated using the synthetic heart rate signal.

15 Claims, 7 Drawing Sheets

(51) Int. Cl.
  *G01S 15/89* (2006.01)
  *A61B 8/14* (2006.01)
  *G01S 7/52* (2006.01)

(52) U.S. Cl.
  CPC ............... *A61B 8/145* (2013.01); *A61B 8/4488* (2013.01); *A61B 8/466* (2013.01); *A61B 8/469* (2013.01)

(56) References Cited

U.S. PATENT DOCUMENTS

| | | |
|---|---|---|
| 6,299,579 B1 | 10/2001 | Peterson et al. |
| 6,436,048 B1 | 8/2002 | Pesque |
| 6,709,994 B2 | 3/2004 | Miller et al. |
| 6,966,878 B2 * | 11/2005 | Schoisswohl et al. ......... 600/443 |
| 7,031,504 B1 | 4/2006 | Argiro et al. |
| 7,131,947 B2 | 11/2006 | Demers |
| 7,261,695 B2 | 8/2007 | Brekke et al. |
| 7,981,037 B2 | 7/2011 | Murashita |
| 2004/0092816 A1 | 5/2004 | Ossmann et al. |
| 2005/0203393 A1 | 9/2005 | Brekke |
| 2005/0234320 A1 | 10/2005 | Balasubramanian |
| 2006/0280284 A1 | 12/2006 | Sasaki et al. |
| 2007/0167809 A1 | 7/2007 | Dala-Krishna |
| 2009/0018448 A1 | 1/2009 | Seo et al. |
| 2012/0123267 A1 | 5/2012 | Dow |

FOREIGN PATENT DOCUMENTS

| | | |
|---|---|---|
| JP | 2009119250 A | 4/2009 |
| WO | 9502361 A1 | 1/1995 |
| WO | 2008071454 A2 | 6/2008 |
| WO | 2011001309 A1 | 1/2011 |

OTHER PUBLICATIONS

Karadayi K et al: "Automatic Image-based Gating for 4D Ultrasound", Conference Proceedings. Annual International Conference of the IEEE Engineering in Medicine and Biology Society (IEEE Cat. No. 06CH37748); Aug. 30-Sep. 3, 2006; New York, NY, USA, IEEE, Piscataway, NJ, USA, Aug. 30, 2006, pp. 1-15.

Deng J et al: "Online motion-gated dynamic three-dimensional echocardiography in the fetus-preliminary results", Ultrasound in Medicine and Biology, New York, NY, US, vol. 27, No. 1, XP004295664, ISSN: Jan. 1, 2001, pp. 43-50.

Deng J et al: "Simultaneous use of two ultrasound scanners for motion-gated three-dimensional fetal echocardiography", Ultrasound in Medicine and Biology, New York, NY, US, vol. 26, No. 6, Jul. 1, 2000, pp. 1021-1032. XP004295636, ISSN: 0301-5629.

Brekke S et al: "2H-6 Tissue Doppler Gated (TDOG) Real-Time Stitching in Three-Dimensional Fetal Echocardiography", Ultrasonics Symposium, 2006. IEEE, IEEE, PI, Oct. 1, 2006, pp. 764-767.

Deng J et al: "Conversion of umbilical arterial doppler waveforms to cardiac cycle triggering signals: a preparatory study for online motion-gated three-dimensional fetal echocardiography", Ultrasound in Medicine and Biology, New York, NY, US, vol. 27, No. 1, Jan. 1, 2001, pp. 51-59, XP004295664.

* cited by examiner

AUTOMATED HEART RATE DETECTION FOR 3D ULTRASONIC FETAL IMAGING

This invention relates to medical diagnostic systems and, in particular, to ultrasonic diagnostic imaging systems for diagnosing the fetal heart by three dimensional (3D) imaging.

Ultrasound is well suited for fetal imaging because it performs noninvasive imaging without exposing either the mother or the fetus to ionizing radiation. An objective of many fetal examinations is to assess the development of the fetal anatomy to determine whether the fetus is developing normally. As ultrasound image quality has improved over the years, more areas of the anatomy can be visualized for development assessment and in greater detail. Consequently fetal ultrasound exams have become more thorough with increased requirements for anatomy which is to be inspected. One area of the anatomy which is greatly scrutinized is the developing fetal heart. In recent years the outflow tracts of the heart have become a focus of greater attention. The cardiac outflow tracts of the fetal heart can be difficult to image, however. One reason for this is the small size of this fetal anatomy. Another reason is that it is desirable to not simply view the anatomy, but also the dynamics of the flow characteristics through the outflow tracts over the full fetal heart cycle. A further reason is that the outflow tracts undergo considerable development as the fetus grows, and consequently can have varying appearances and complexity depending on fetal age. The outflow tracts can thus be difficult to identify on the ultrasound display, and it can be even more difficult to acquire an image frame of the proper orientation for an adequate diagnosis.

Some of these demands have been eased by the recent use of 3D ultrasound to image the fetal heart. With 3D imaging, the full fetal heart can be imaged and a sequence of 3D image data sets can be acquired for later replay and diagnosis. When data of the full fetal heart is acquired in the data sets, the image data can be examined during post-acquisition diagnosis to locate the outflow tracts of the heart. Different varying 2D image planes can be extracted from the 3D data in multiplanar reconstruction (MPR), so that an image plane of a desired orientation can be examined. Three dimensional imaging thus addresses many of the static imaging challenges which are problematic with 2D fetal imaging. Recently the problem of analyzing the temporal dynamics of fetal blood flow have been addressed by a technique called "spatial-temporal image correlation," or STIC. With STIC, a sweep is made through the fetal heart with ultrasound and many image frames are acquired over a sequence of heart cycles. When done by manually scanning with a 2D ultrasound probe, this image acquisition can take ten seconds or longer. The same acquisition can be performed with a mechanical 3D probe which mechanically sweeps the image plane through the fetal heart region, but 3D mechanical probes often have poorer elevation focus which leads to inaccuracies when constructing MPR images in the elevation dimension. After the acquisition is complete and the image frames are stored, image frames of the desired anatomy, created by MPR reconstruction if necessary, are reassembled into a loop of images according to their phase sequence in the fetal heart cycle. This task is made difficult by the fact that no ECG signal of the fetal heart is available for this reordering. A fetal ECG cannot be acquired during imaging since ECG electrodes cannot be attached to the fetus and the fetal electrical impulses are overwhelmed by the mother's own ECG signals. Consequently it is necessary to extract a synthetic timing signal of the fetal heart cycle from the fetal heart images. This is done by determining event triggers based on fetal tissue movement at or near the heart as described in U.S. Pat. No. 7,261,695 (Brekke et al.) The synthetic heart cycle trigger signals are then used to reorder the images from multiple heart cycles into one loop of a heart cycle in which the frames are in heart beat phase order.

The STIC technique is not without its difficulties however. One is the robustness of the reassembly algorithm. Since the typical acquisition creates far too many images to reorder manually, algorithms have been developed to do the reordering of the frames automatically. These algorithms are dependent upon image data quality, which can be less than adequate. Efforts have been made to improve this situation by using recommended manipulation of the probe to acquire optimal data sets, but this is technique-dependent and its use of anatomical statistics can cause it to be individual patient-dependent. But a greater problem is that the fetus frequently moves and may not remain stationary during the full ten or more seconds needed for data acquisition. When the fetus moves the orientation of the desired image data relative to the probe will change, and may leave the field of view entirely, resulting in an absence of the desired anatomy from the acquired data set. Also, fetal movement during the acquisition limits the accuracy of the derived synthetic fetal heart cycle, which introduces artifacts into the reconstructed 3D data.

An alternative to STIC which addresses these problems is described in U.S. patent application No. 61/221,885, filed Jun. 30, 2009 by Jago et al. and entitled THREE DIMENSIONAL FETAL HEART IMAGING BY NON-ECG PHYSIOLOGICAL GATED ACQUISITION. In that application, a diagnostic ultrasound system is described which acquires 3D fetal heart data sets gated to the fetal heart cycle by a physiologically derived gating signal. The fetal heart is imaged by either 1D, 2D or 3D imaging and echo signals from a target exhibiting suitable motion are acquired. For fetal heart imaging the target could be the heart muscle of the fetus or motion of blood in the fetal carotid artery, for example. The motion signals are processed to produce a gating signal synchronized to the fetal heart cycle, which is used to gate 3D image data acquisition. Three dimensional data sets are then acquired in timed relation to the phase of the fetal heartbeat using this physiologically derived gating signal. Gating of acquisition in 3D is much easier to achieve with a 2-dimensional matrix transducer incorporating a micro-beamformer, since in this case imaging planes can be generated electronically in any sequence or orientation. Using such a matrix transducer, a loop of a heart cycle can generally be acquired in less than one second and several loops can be acquired in only a few seconds. Since the acquired image data is already in phase with the fetal heart cycle there is no need to reorder the image data, and since the acquisition takes only a few seconds, fetal movement is less of a concern. One other advantage of this approach, compared to STIC, is that the user can be presented with reconstructed images that show the quality of the acquisition, so that the use can decide if any motion artifacts are present before completing the data acquisition. If the fetus does move during the short acquisition interval the probe can be repositioned and another 3D data acquisition performed. The successfully acquired 3D data can thereafter be carefully analyzed during post-acquisition diagnosis. It is desirable to provide a workflow for the clinician which makes such a system easy to use. In particular it is desirable for the system workflow to easily and reliably acquire the physiologically derived gating signal, to know when a stable gating signal is being produced, and to enable the clinician to promptly acquire the desired loops of the fetal heart with the gating signal.

In accordance with the principles of the present invention, a diagnostic ultrasound has a workflow and controls which facilitate acquisition of a loop of 3D fetal heart images with a synthetically derived heart gating signal. The heart rate is derived during 3D imaging without the need to exit to another imaging mode. The workflow enables the clinician to set a 3D region of interest (ROI) about the fetal heart, then automatically acquire the fetal heart rate. When the clinician presses the "triggered" control, the system begins to acquire the fetal heart rate, and provides feedback to the clinician when a suitable heart rate signal is being acquired. The clinician then presses a "start" control to initiate triggered 3D acquisition. Within a second or two the triggered 3D image acquisition is complete and the image loops are ready for post-acquisition analysis.

Figure 1:
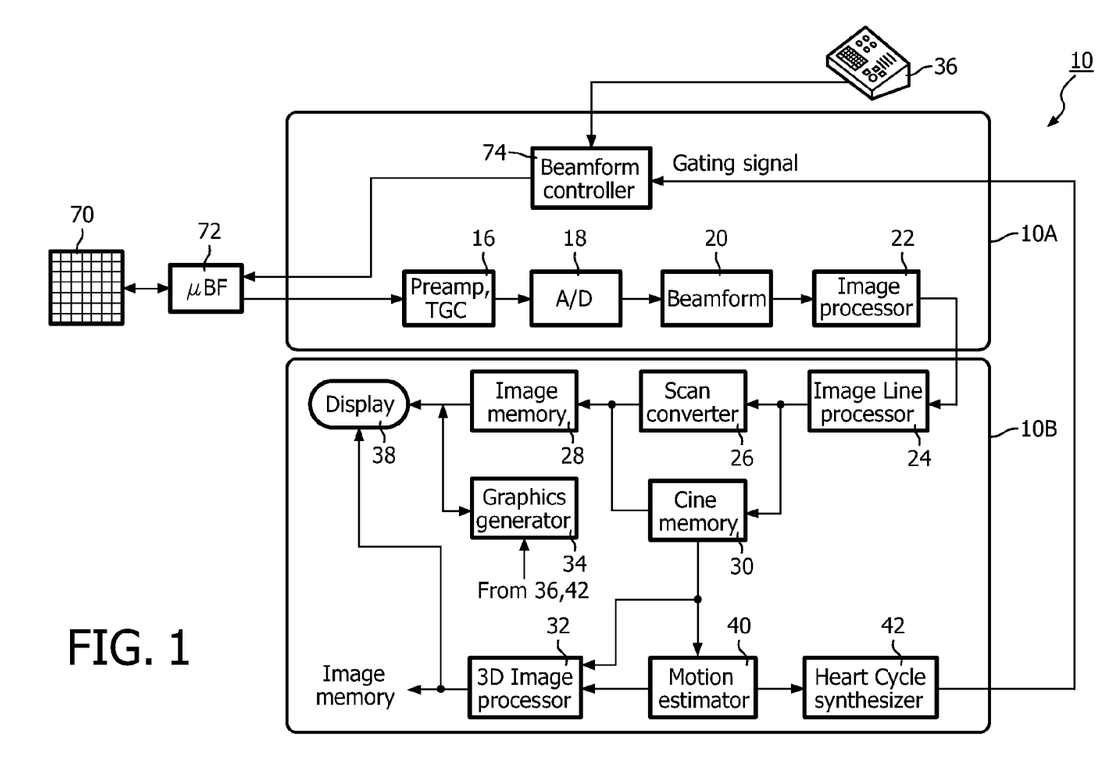
FIG. 1 illustrates in block diagram form an ultrasonic diagnostic imaging system constructed in accordance with the principles of the present invention.

Referring first to FIG. 1, an ultrasound system 10 constructed in accordance with the principles of the present invention is shown in block diagram form. The ultrasound system is configured by two subsystems, a front end acquisition subsystem 10A and a display subsystem 10B. An ultrasound probe is coupled to the acquisition subsystem which includes a two-dimensional matrix array transducer 70 and a micro-beamformer 72. The micro-beamformer contains circuitry which control the signals applied to groups of elements ("patches") of the array transducer 70 and does some processing of the echo signals received by elements of each group. Micro-beamforming in the probe advantageously reduces the number of conductors in the cable between the probe and the ultrasound system and is described in U.S. Pat. No. 5,997,479 (Savord et al.) and in U.S. Pat. No. 6,436,048 (Pesque).

The probe is coupled to the acquisition subsystem 10A of the ultrasound system. The acquisition subsystem includes a beamform controller 74 which is responsive to a user control 36 and provides control signals to the microbeamformer 72, instructing the probe as to the timing, frequency, direction and focusing of transmit beams. The beamform controller also control the beamforming of echo signals received by the acquisition subsystem by its control of analog-to-digital (A/D) converters 18 and a beamformer 20. Echo signals received by the probe are amplified by preamplifier and TGC (time gain control) circuitry 16 in the acquisition subsystem, then digitized by the A/D converters 18. The digitized echo signals are then formed into fully steered and focused beams by a beamformer 20. The echo signals are then processed by an image processor 22 which performs digital filtering, B mode and M mode detection, and Doppler processing, and can also perform other signal processing such as harmonic separation, speckle reduction, and other desired image signal processing.

The echo signals produced by the acquisition subsystem 10A are coupled to the display subsystem 10B, which processes the echo signals for display in the desired image format. The echo signals are processed by an image line processor 24, which is capable of sampling the echo signals, splicing segments of beams into complete line signals, and averaging line signals for signal-to-noise improvement or flow persistence. The image lines for a 2D image are scan converted into the desired image format by a scan converter 26 which performs R-theta conversion as is known in the art. The image is then stored in an image memory 28 from which it can be displayed on a display 38. The image in memory is also overlaid with graphics to be displayed with the image, which are generated by a graphics generator 34 which is responsive to the user control 36. Individual images or image sequences can be stored in a cine memory 30 during capture of image loops or sequences.

For real-time volumetric imaging the display subsystem 10B also includes a 3D image rendering processor 32 which receives image lines from the image line processor 24 for the rendering of real-time three dimensional images. The 3D images can be displayed as live (real time) 3D images on the display 38 or coupled to the image memory 28 for storage of the 3D data sets for later review and diagnosis.

Figure 7:
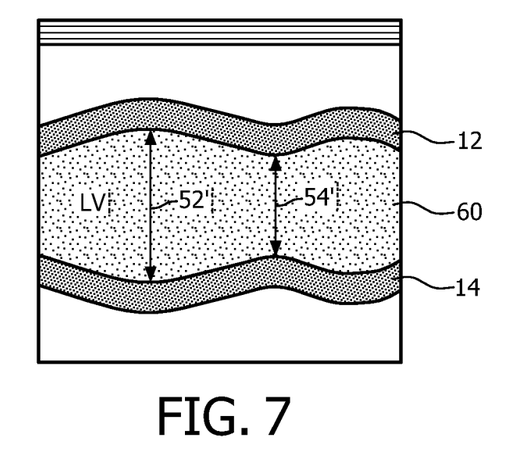
FIG. 7 illustrates one technique for automatically acquiring a fetal heart trigger signal.

In accordance with the principles of the present invention a fetal heart rate synthesizer produces a heart rate trigger signal for gated 3D acquisition of fetal heart images. In the implementation of FIG. 1, the fetal heart rate synthesizer comprises a motion estimator 40 which receives temporally discrete echo signals from a designated location of the imaged anatomy, an ROI, and processes the echoes to produce a signal representative of motion at the designated location. The location in the anatomy from which the temporally discrete echo signals are acquired can be a default image location such as the center of the image, or it can be a location designated by the user by manipulation of a control of the user controls 36. For instance, the user can manipulate a joystick, trackball, or other control of the user controls to locate a sample volume in the carotid artery of the fetus. Motion estimation can then be performed from samples of the moving fetal tissue or blood. Some of this processing may be performed by the image processor, such as Doppler processing of echo signals from the sample volume location. Flow or tissue motion velocity estimates produced by the image processor can then be forwarded directly to the motion estimator, for example. If the sample volume is placed on tissue such as the fetal heart muscle, the echo signals from the fetal heart can be processed for motion discrimination by tissue Doppler processing. Another way to detect motion is by tracking the movement of speckle at a given tissue location in the image. Yet another way to detect motion is by comparing changes in tissue location over consecutive images by MSAD block matching as described in U.S. Pat. No. 6,299,579 (Peterson et al.) Still another technique for detecting motion is to use M mode with the M line positioned through the fetal heart. This is illustrated in FIG. 7, which shows an M mode image 60 produced by an M line located by positioning the M line cursor on the ultrasound image so that it extends through the left ventricle (LV) of the fetal heart. When positioned in this manner the M line will pass through the myocardial wall 12 on one side of the fetal heart, through the chamber of the LV, and through the myocardial tissue 14 on the other side of the heart. An ultrasound beam is transmitted along this M line direction through the LV periodically, and the received A-line from each transmission is shown on the display in a scrolling manner along the previously received A-lines. The result is an M mode image as shown in FIG. 7 where the opposite sides of the heart are most greatly separated when the fetal heart is relaxed at the end diastole point in the heart cycle as indicated by arrow 52'. The opposite walls of the heart are in closest proximity at the peak systole phase of the heart cycle as indicated by arrow 54'. FIG. 7 illustrates this cyclical pattern of the movement of the heart wall as the fetal heart contracts and expands with each heart beat. By tracking the changing position (motion) of the heart wall 12 or 14, a waveform in phase with the heart cycle can be produced by a heart cycle synthesizer 42 coupled to receive the fetal heart motion signals.

Other techniques of fetal heart rate detection such as frequency estimation of the fetal heart motion with peak frequency detection can also be used to develop a heart rate trigger signal. Once a trigger signal has been produced by these or any other technique, the heart rate trigger signal is applied to the beamformer controller 74 where it is used to gate the acquisition of fetal heart images. The heart rate signal is also coupled to the graphics generator 34 where it may be displayed as feedback to the user as discussed more fully below.

Figure 2:
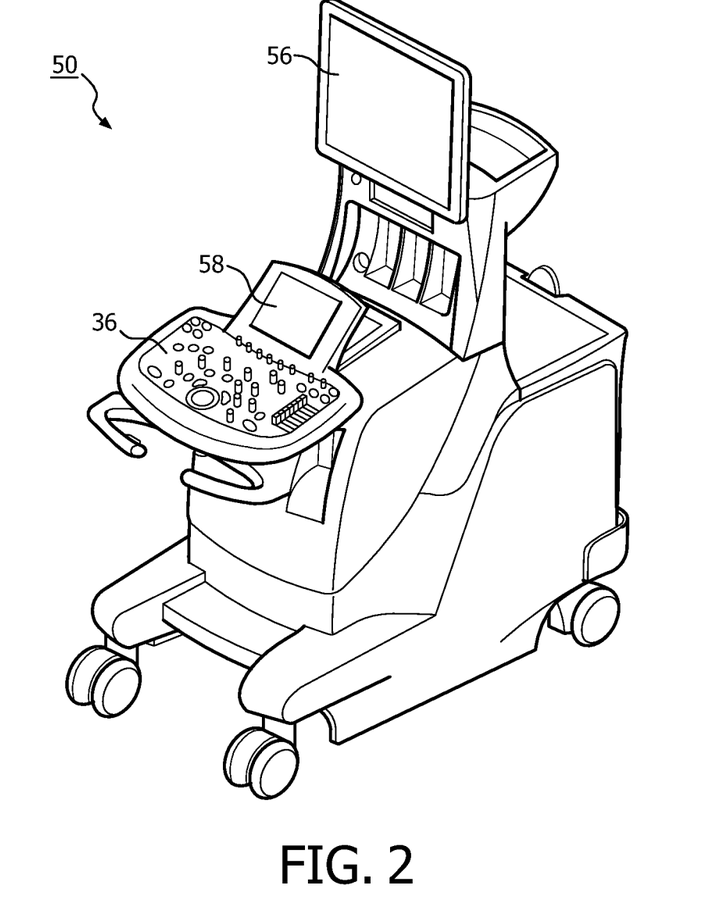
FIG. 2 illustrates a typical ultrasound system on which a 3D fetal heart imaging system of the present invention has been implemented.

FIG. 2 illustrates an ultrasound system 50 on which an embodiment of the present invention has been implemented. The system 50 includes a display 56 on which the acquired ultrasound images are displayed. Control of the ultrasound system is provided in two ways. One is the control panel 36 at the front of the system, which includes the trackball, buttons, and controls used for basic system operation. A touch screen display 58 is at the top of the control panel and displays softkeys for advanced features which can be changed periodically or for each step of a procedure. The softkeys of the touch screen display 58 are used extensively in the implementation of the present invention as described below.

Figure 3:
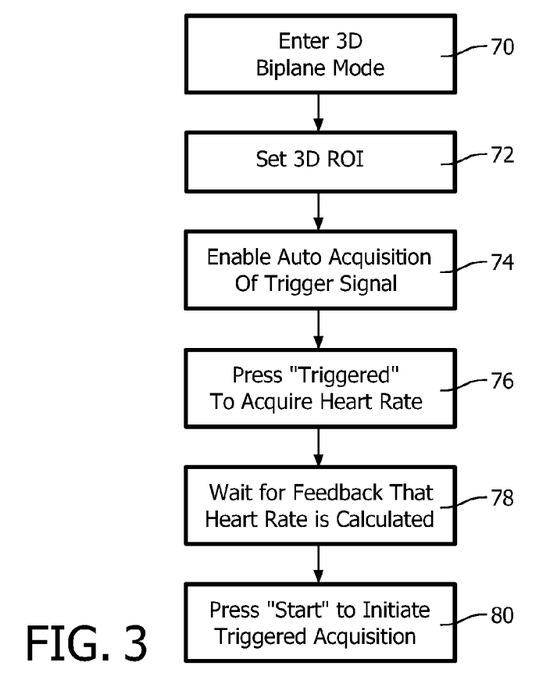
FIG. 3 is a flowchart of a workflow of the present invention for acquiring a trigger signal for fetal heart imaging, then using the trigger signal for 3D image acquisition.
Figure 4:
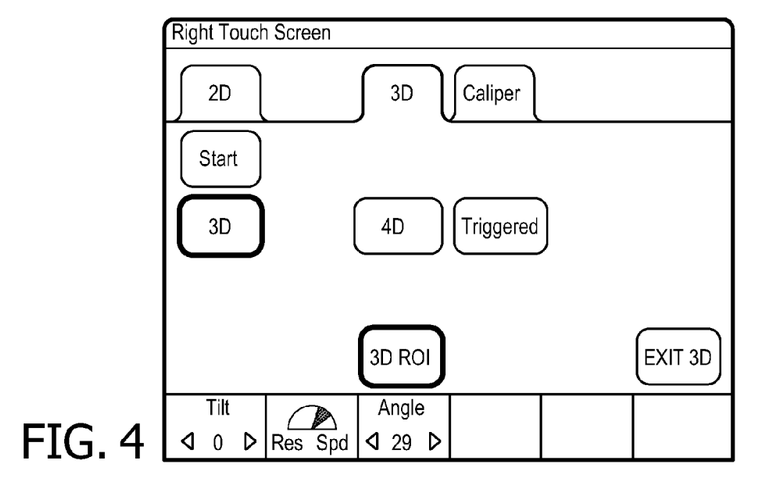
FIG. 4 illustrates a control panel in accordance with the present invention for setting an ROI of the fetal heart.
Figure 5:
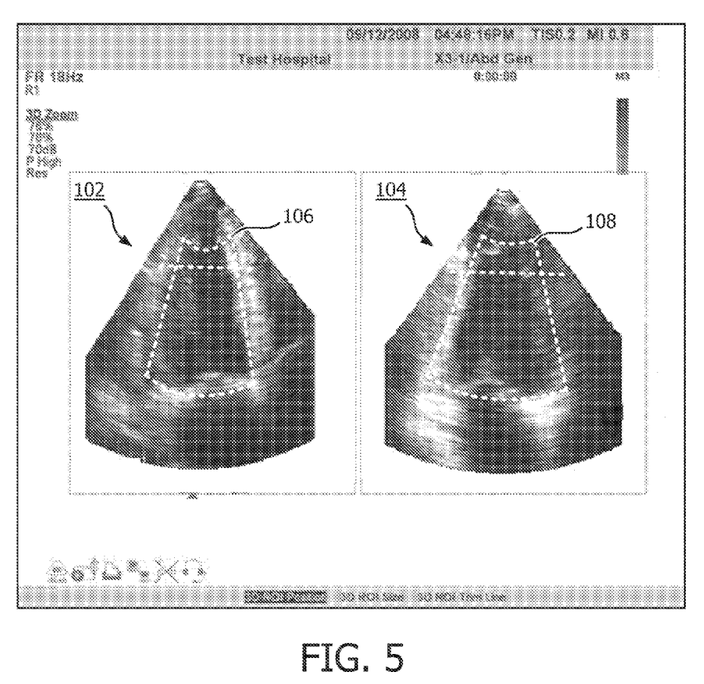
FIG. 5 illustrates a 3D display which is suitable for use in carrying out the fetal heart acquisition workflow of the present invention.

FIG. 3 is a flow chart showing the sequence of workflow of an implementation of the present invention. This workflow sequence begins with a step 70 when the sonographer touches a softkey button on the touch screen display to enter the 3D biplane mode from the normal 3D imaging mode. FIG. 4 illustrates the touch screen buttons displayed when the sonographer has entered the biplane mode. The 3D biplane mode is described in U.S. Pat. No. 6,709,994 (Frisa et al.), and is a mode in which two planes of a volumetric region of the body are alternately imaged in rapid succession, thereby producing live images of each plane of the body. When the imaging system first enters the biplane mode, two images aligned with the center of the 2D array transducer and of orthogonal planes are scanned and displayed. With the biplane images shown on the image display 56, the sonographer in step 72 touches the "3D ROI" button shown on the touch screen display of FIG. 4 at the bottom of the screen. This button turns on a dashed ROI outline on each biplane image which is produced by the graphics generator 34. FIG. 5 illustrates two biplane images 102 and 104, each with a dashed trapezoidal ROI outline 106, 108 in the center of the image. When the fetal heart is positioned in the center of the initial 3D image, the two ROI outlines 106 and 108 will each define a region of interest which includes the fetal heart in the center of each biplane image 102 and 104.

Figure 6A:
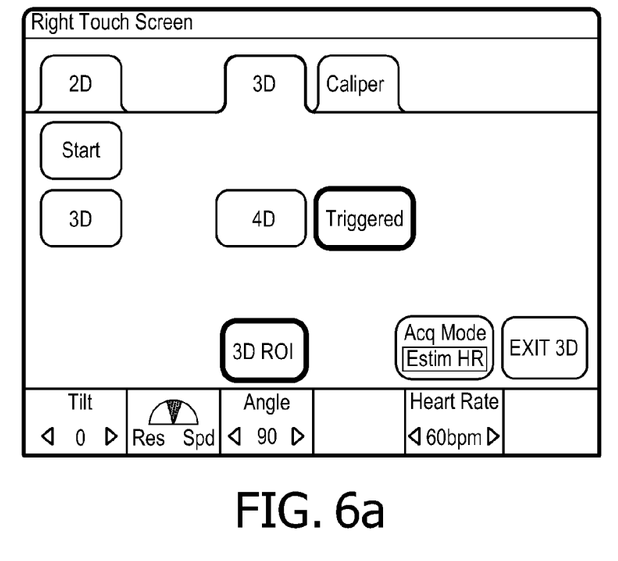
FIGS. 6a and 6b illustrate a control panel for optionally acquiring a trigger signal either manually or automatically.
Figure 6B:
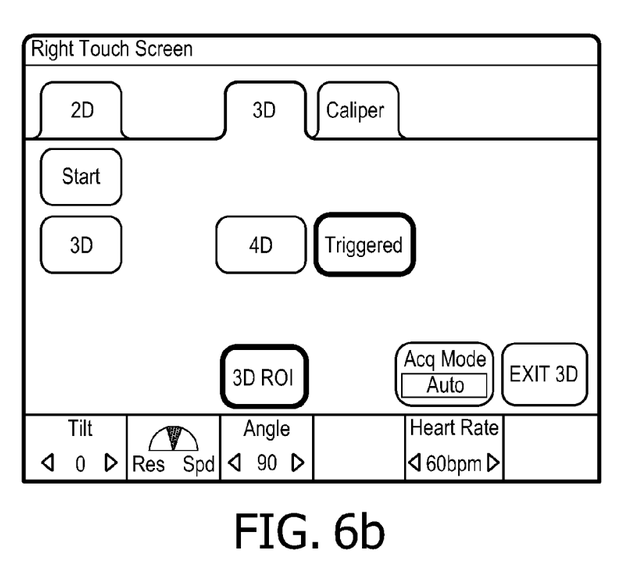

With the fetal heart thus indicated by the ROIs, the sonographer enables auto-acquisition of a trigger signal in step 74 for gated acquisition of 3D images of the fetal heart. The sonographer first determines whether a manually set heart rate or an automatically determined heart rate is to be used for gated acquisition. This is done by setting an auto-acquisition mode button to the desired mode as shown by the "Acq Mode" button in FIGS. 6a and 6b. This button has two modes of operation, one in which the sonographer sets the heart rate manually (FIG. 6a), and another where the trigger signal is automatically acquired (FIG. 6b). When the manual mode has been selected, the notation "Estim HR" appears on the "Acq Mode" button as seen in FIG. 6a. The sonographer then sets the heart rate manually by tapping on incrementing and decrementing arrows on either side of the heart rate number of the "Heart Rate" button just below the "Acq Mode" button. In the example of FIG. 6a the heart rate value has been set to 60 bpm. The sonographer may elect to set the heart rate to the value previously indicated by the M mode display of heart motion, for instance.

If the "Acq Mode" button is in the manual mode, the sonographer can touch the button to toggle to the automatic mode, in which case "Auto" appears on the "Acq Mode" button as shown in FIG. 6b. The sonographer then touches the "Triggered" button above the "Acq Mode" button to acquire the fetal heart rate automatically as indicated by step 76 in FIG. 3. The system then begins to estimate the fetal heart rate automatically by use of, for instance, one of the measurement techniques described above. As the system does this, the current automatically estimated heart rate value appears on the "Heart Rate" button and changes as the system updates its estimate of the fetal heart rate. When the estimate becomes stable, the system is ready for triggered acquisition of 3D fetal heart images. This stability is indicated by audible or visual feedback as indicated in step 78. For example, the dashed ROI outline can be one color initially (e.g., white or yellow) and can change to a second color (e.g., green) when the automatically detected heart rate has become stable. Another alternative is for the number of beats per minute on the "Heart Rate" button to turn green when the estimated heart rate has become stable. When the detected heart rate has become stable, the sonographer touches the "Start" button (step 80 of FIG. 3) at the upper left of the touch screen display 58 as seen in FIG. 6b. The ultrasound system will then use the automatically determined trigger signal to acquire gated 3D fetal images over a number of heartbeats, such as four heartbeats. The acquired images are stored and are ready for subsequent replay and diagnosis.

Figure 8:
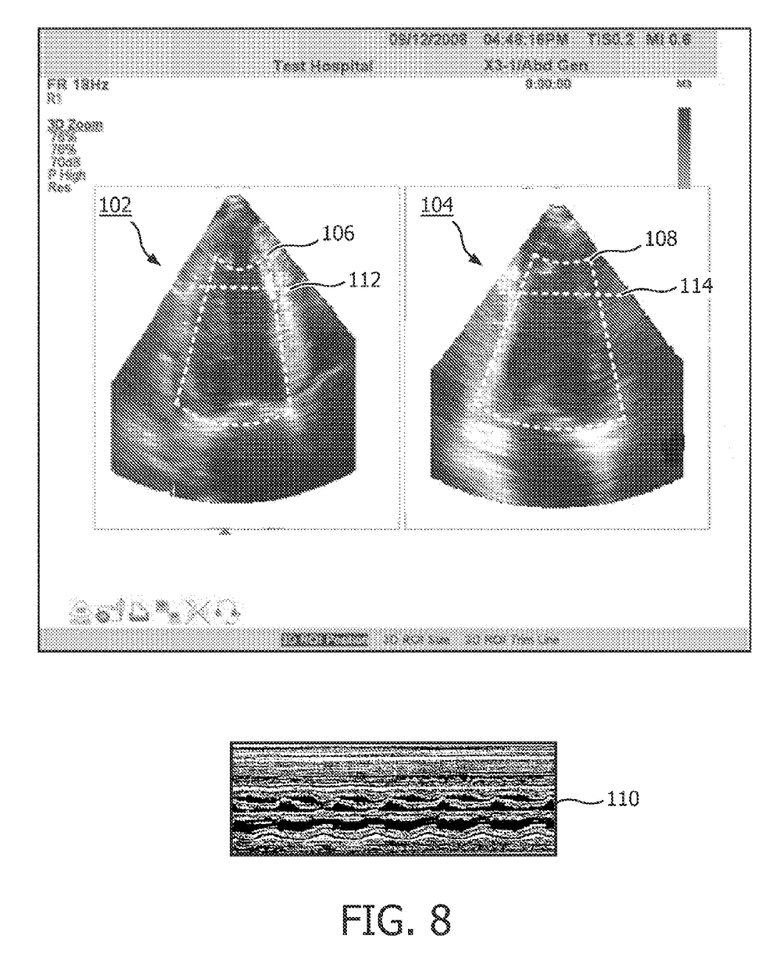
FIG. 8 illustrates a 3D display which additionally displays an M mode image which supports and provides user confidence in the synthetically derived fetal heart rate signal.

At the end of 3D image acquisition, the constructed system displays the biplane images 102, 104 as shown in FIG. 8 with an M mode display 110 below the biplane images. A M line such as M line 112 or M line 114 indicates the location in the anatomy where the M mode display was acquired. The sonographer can have confidence in the automatically acquired gated 3D images by viewing the M mode display 110, which was acquired at the same time as the gated 3D images. When the M mode display shows a steady cyclical pattern of heart motion, the sonographer can be confident that the trigger signal estimated from the M mode display was stable and suitable for use as a fetal gating signal.

What is claimed is:

1. An ultrasonic diagnostic imaging system for gated acquisition of 3D fetal heart images, the system comprising:
   an ultrasound probe including a two dimensional array transducer adapted for 3D fetal imaging;
   an image processor adapted to process image signals from the probe for display;
   an image display coupled to the image processor;
   a graphics generator responsive to a user control adapted to identify a region of interest (ROI) in an ultrasound image, the user control being adapted to initiate processing of ultrasound data identified by the ROI to determine a fetal heart rate;

an indicator responsive to the processing of ultrasound data to determine a fetal heart rate which indicates that a fetal heart rate has been determined; and an acquisition control adapted to be actuated by a user to acquire gated 3D fetal heart images in synchronism with the fetal heart rate when the indicator indicates that the fetal heart rate has been determined.

2. The ultrasonic diagnostic imaging system of claim 1, wherein the user control adapted to initiate processing of ultrasound data identified by the ROI is further adapted to actuate a heart cycle synthesizer responsive to echo signals received from the ROI to produce a synthetic fetal heart rate signal.

3. The ultrasonic diagnostic imaging system of claim 2, wherein the heart cycle synthesizer is responsive to estimates of motion produced by a motion estimator in response to echo signals received from the ROI.

4. The ultrasonic diagnostic imaging system of claim 2, wherein the heart cycle synthesizer is responsive to estimates of frequency produced in response to echo signals received from the ROI.

5. The ultrasonic diagnostic imaging system of claim 1, wherein the indicator produces a visual or audible indication when a fetal heart rate has been determined.

6. The ultrasonic diagnostic imaging system of claim 5, wherein the indicator produces a visual indication in conjunction with the display of an ultrasound image.

7. The ultrasonic diagnostic imaging system of claim 5, wherein the visual indication is produced in conjunction with the user control.

8. The ultrasonic diagnostic imaging system of claim 1, wherein the acquisition control is further adapted to acquire gated 3D fetal heart images for a plurality of heart cycles in synchronism with the determined fetal heart rate.

9. The ultrasonic diagnostic imaging system of claim 1, wherein the user control is adapted such that a user can manually set a fetal heart rate.

10. A method for acquiring 3D fetal heart images gated by a synthetic fetal heart rate signal, the method comprising:
    acquiring ultrasound images of a fetal heart;
    defining a region of interest (ROI) in an ultrasound image which delineates the fetal heart in the image;
    using echo signals returned from the ROI to automatically estimate the fetal heart rate;
    producing an indication that the fetal heart rate has been estimated; and
    following the indication that the fetal heart rate has been estimated, acquiring gated 3D fetal heart images in synchronism with the estimated fetal heart rate.

11. The method of claim 10, wherein producing an indication further comprises producing an audible or visual indication that a stable fetal heart rate has been estimated.

12. The method of claim 10, wherein using echo signals to automatically estimate the fetal heart rate further comprises estimating the fetal heart rate by one of motion estimation or frequency estimation.

13. The method of claim 10, wherein acquiring further comprises acquiring biplane images of the fetal heart;
    wherein defining an ROI further comprises defining an ROI in each biplane image.

14. The method of claim 10, wherein acquiring gated 3D fetal heart images further comprises acquiring gated 3D fetal heart images for a plurality of fetal heart cycles.

15. The method of claim 10, further comprising displaying an ultrasound image with an ROI defined therein, together with an M mode image produced from ultrasound echo signals received from the ROI.

* * * * *